(12) United States Patent
Simon

(10) Patent No.: US 10,022,203 B2
(45) Date of Patent: Jul. 17, 2018

(54) HANDPIECE FOR ENDODONTIC TREATMENT

(71) Applicant: ITENA CLINICAL, Paris (FR)

(72) Inventor: Stéphane Simon, Rouen (FR)

(73) Assignee: ITENA CLINICAL, Paris (FR)

( * ) Notice: Subject to any disclaimer, the term of this patent is extended or adjusted under 35 U.S.C. 154(b) by 373 days.

(21) Appl. No.: 14/405,648

(22) PCT Filed: Jun. 4, 2013

(86) PCT No.: PCT/EP2013/061495
§ 371 (c)(1),
(2) Date: Dec. 4, 2014

(87) PCT Pub. No.: WO2013/182563
PCT Pub. Date: Dec. 12, 2013

(65) Prior Publication Data
US 2015/0125812 A1    May 7, 2015

(30) Foreign Application Priority Data

Jun. 5, 2012    (FR) ...................................... 12 55232

(51) Int. Cl.
| | | |
|---|---|---|
| *A61C 5/02* | (2006.01) | |
| *A61C 1/14* | (2006.01) | |
| *A61C 1/12* | (2006.01) | |
| *A61C 1/00* | (2006.01) | |
| *A61C 5/40* | (2017.01) | |
| *A61C 5/42* | (2017.01) | |

(52) U.S. Cl.
CPC ............ *A61C 5/023* (2013.01); *A61C 1/0084* (2013.01); *A61C 1/12* (2013.01); *A61C 1/141* (2013.01); *A61C 5/40* (2017.02); *A61C 5/42* (2017.02); *A61C 2204/002* (2013.01)

(58) Field of Classification Search
CPC ......... A61C 5/023; A61C 5/02; A61C 1/0084; A61C 1/141; A61C 1/12; A61C 2204/002
USPC ............................................. 433/224, 80–90
See application file for complete search history.

(56) References Cited

U.S. PATENT DOCUMENTS

| | | | |
|---|---|---|---|
| 5,404,608 A * | 4/1995 | Hommann | A61C 17/3445 15/22.1 |
| 5,725,370 A | 3/1998 | Himeno et al. | |

(Continued)

FOREIGN PATENT DOCUMENTS

| | | |
|---|---|---|
| EP | 1 743 593 A1 | 1/2007 |
| FR | 2 466 236 A1 | 4/1981 |
| JP | 2004-313659 A | 11/2004 |

OTHER PUBLICATIONS

International Search Report dated Sep. 3, 2013 issued in corresponding application No. PCT/EP2013/061495, and written opinion; with English partial translation and partial machine-translation.

*Primary Examiner* — Matthew Nelson
(74) *Attorney, Agent, or Firm* — Westerman, Hattori, Daniels & Adrian, LLP

(57) ABSTRACT

Handpiece (1) for endodontic treatment, characterized in that it comprises an irrigation device for conveying an irrigation solution from a reservoir (10) to a head (5) for the purpose of ejecting the solution into a root canal, and in that it comprises an agitator device for setting in motion an endpiece (2) intended to penetrate inside a root canal in order to promote the action of the irrigation solution.

25 Claims, 8 Drawing Sheets

(56) References Cited

U.S. PATENT DOCUMENTS

| | | | |
|---|---|---|---|
| 6,579,092 B1* | 6/2003 | Senia | A61C 5/42 |
| | | | 433/102 |
| 7,261,561 B2 | 8/2007 | Ruddle et al. | |
| 2005/0255426 A1* | 11/2005 | Mariaulle | A61C 1/0061 |
| | | | 433/98 |
| 2007/0015108 A1 | 1/2007 | Ruddle et al. | |
| 2007/0275347 A1* | 11/2007 | Gruber | A61C 17/22 |
| | | | 433/80 |
| 2009/0042163 A1 | 2/2009 | Johnson | |
| 2010/0092922 A1 | 4/2010 | Ruddle | |
| 2011/0223555 A1* | 9/2011 | Thoms | A61C 3/025 |
| | | | 433/29 |
| 2011/0262879 A1* | 10/2011 | Hegemann | A61C 17/0202 |
| | | | 433/82 |
| 2012/0016262 A1* | 1/2012 | Hibner | A61B 10/0275 |
| | | | 600/566 |
| 2012/0064480 A1* | 3/2012 | Hegemann | A61C 17/0202 |
| | | | 433/82 |
| 2012/0308956 A1* | 12/2012 | DeVengencie | A61C 3/03 |
| | | | 433/86 |
| 2013/0040267 A1* | 2/2013 | Bergheim | A61C 3/03 |
| | | | 433/216 |

* cited by examiner

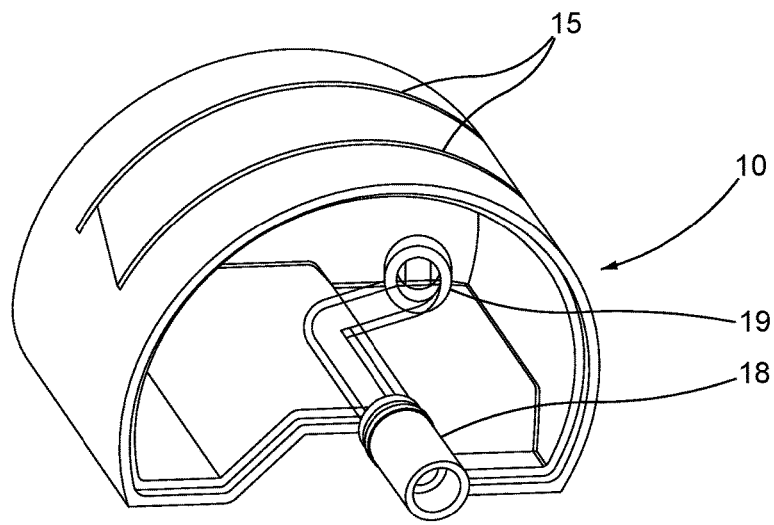
FIG.6
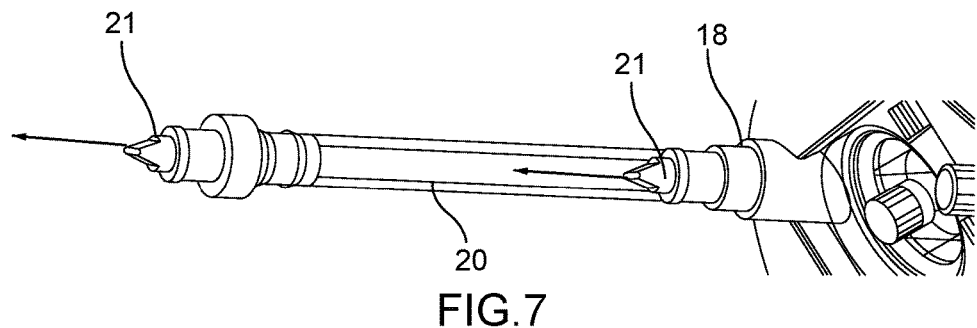
FIG.7
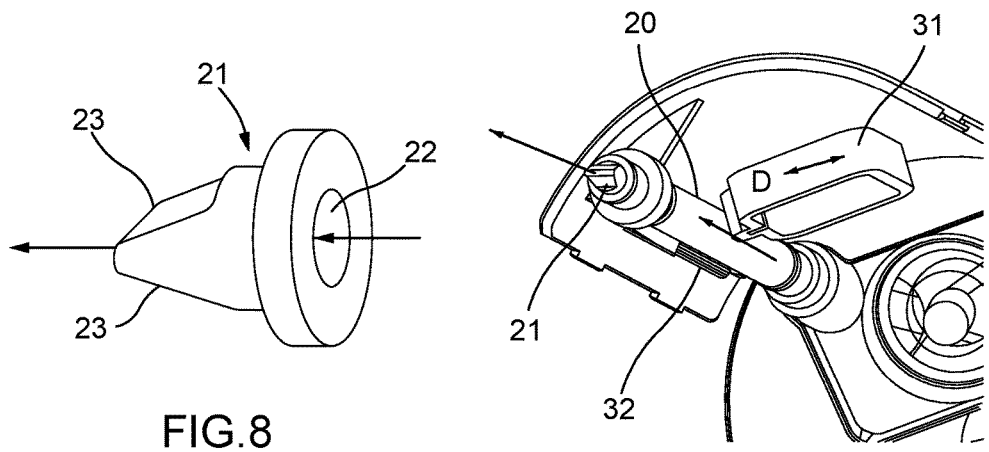
FIG.8
FIG.9

Pic. A   Pic. B   Pic. C

HANDPIECE FOR ENDODONTIC TREATMENT

The present invention relates to a handpiece for dental treatment, more particularly for endodontic treatment, and to a special endpiece adapted for such a handpiece.

Endodontics concerns the treatment of the root canals. For this treatment, instruments have been developed that permit cleaning of the canals by removing in particular the pulp and the bacteria located therein. These instruments also have the function of shaping the canals, generally with a conical shape, which can thus be advantageously closed subsequently with a plastic material when this endodontic treatment is finished. The disinfection is insufficient when the canal is treated by the instrument alone, as can be seen from recurrent infections and from the development of associated bone diseases. To be effective, this treatment of the canal by an instrument has to be combined with chemical disinfection, which is provided by using a disinfectant irrigation solution. It is this combination of treatment by an instrument and irrigation of the canal that makes it possible to achieve complete disinfection and prevent associated bone diseases. This irrigation is ensured by the replenishment of solutions injected into the canal with a dedicated needle. To optimize its efficacy, it is recommended that this solution be activated by mechanical agitation. At present, these two steps are implemented by alternate use of two separate appliances. The disadvantage of this approach lies in its overall cost and in the poor ergonomics of the procedures, since it requires complementary and complex devices for its implementation.

In order to improve the ergonomics of the irrigation protocol, the document EP1743593 describes a handpiece with a shape adapted for comfortable manual manipulation by a practitioner, who is able to cause sonic vibration of an endpiece designed to penetrate inside the root canals in order to activate an irrigation solution that is arranged beforehand in these canals, generally a solution of sodium hypochlorite or of EDTA, favourable to disinfection. This handpiece is therefore designed specially for a particular phase of the treatment and aims to trigger a phenomenon of mechanical activation within the canals in order to promote the action of the irrigation solution, without damaging the walls of these canals.

The object of the invention is to make available a solution for carrying out endodontic treatment that is effective, without risk of future reinfection, and that is convenient and simplified.

To this end, the invention relates to a handpiece for endodontic treatment, characterized in that it comprises an irrigation device for conveying an irrigation solution from a reservoir to a head for the purpose of ejecting the solution into a root canal, and in that it comprises an agitator device for setting in motion an endpiece intended to penetrate inside a root canal in order to promote the action of the irrigation solution.

The handpiece is defined more particularly by the claims.

The endpiece can be hollow along at least part of its length, so as to be able to form a conduit for an irrigation solution coming from a reservoir of the handpiece.

These subjects, features and advantages of the present invention will be explained in detail in the following description on the basis of a particular non-limiting embodiment and by reference to the attached figures, in which:

FIG. 6 shows a perspective view of the inside of the reservoir of the handpiece according to the embodiment of the invention.

FIG. 7 shows a perspective view of an irrigation conduit of the handpiece participating in the pumping function according to the embodiment of the invention.

FIG. 8 shows a perspective view of a duckbill joint used in the area of an irrigation conduit of the handpiece according to the embodiment of the invention.

FIG. 9 shows a perspective view of part of the pumping device of the irrigation device of the handpiece according to the embodiment of the invention.

Figure 1:
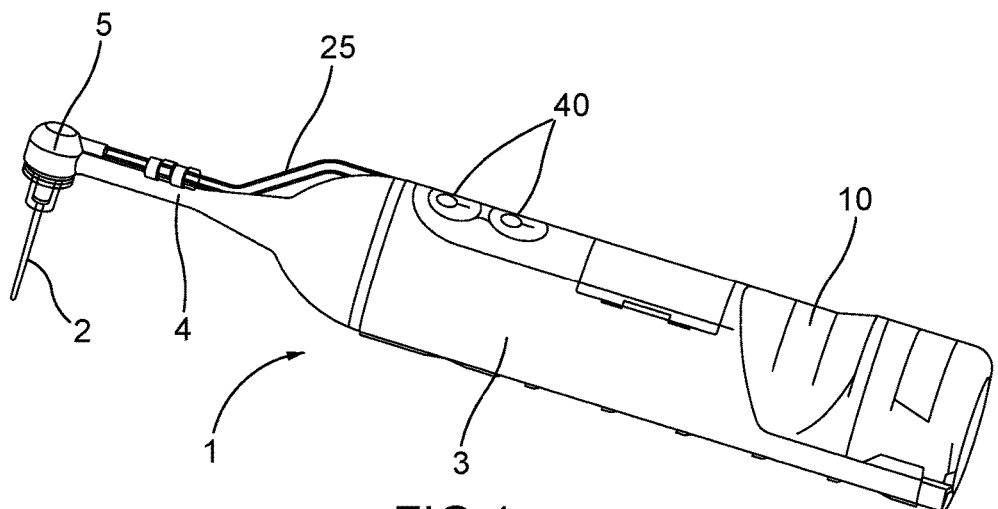
FIG. 1 shows a perspective side view of a handpiece according to an embodiment of the invention.

The handpiece 1 according to the embodiment of the invention, illustrated in FIG. 1, combines within one and the same tool the function of irrigation and the function of agitation of the root canal irrigation solution. It is in two parts. A first, rear part comprises a main body 3, which extends along substantially two thirds of its length and has a rounded, substantially cylindrical outer shape inscribed within a cylinder with a diameter of less than or equal to 5 cm. A second, front part is narrower, with a diameter of less than or equal to 4 cm, and forms a joining arm 4 to a head 5, the latter comprising a connector for an endpiece 2, which extends in a direction substantially perpendicular to the axis of the first part. This arm 4 is designed to position the endpiece 2 in the mouth of a patient, within a root canal, and this is aided by its thin and elongate shape. This handpiece 1 as a whole has an ergonomic shape that is easy to manipulate and similar to an electric toothbrush. To simplify the rest of the description, longitudinal direction will be used to designate a direction parallel to the axis of the main body 3 of the handpiece, and also substantially parallel to the arm 4 in this embodiment, and, following convention, an orientation of the handpiece will be chosen which is such that the front corresponds to the head 5 of the handpiece.

Thus, the handpiece 1 comprises first of all an irrigation device. For this purpose, it comprises a reservoir 10 to contain the stock of irrigation solution, a pumping and ejecting device with which the irrigation solution can be conveyed from this reservoir into the canal, by way of an endpiece 2. It then also comprises an agitator device for setting in motion an endpiece 2 designed to agitate the irrigation solution present in a root canal. These different and complementary devices are now described in detail.

Figure 2:
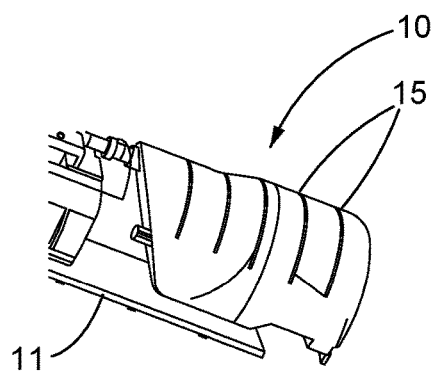
FIG. 2 shows a perspective side view of the rear part of the handpiece comprising a reservoir according to the embodiment of the invention.
Figure 3:
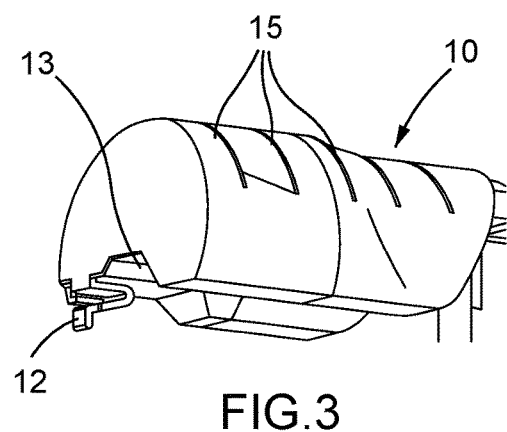
FIG. 3 shows a perspective view of the reservoir of the handpiece according to the embodiment of the invention.
Figure 4:
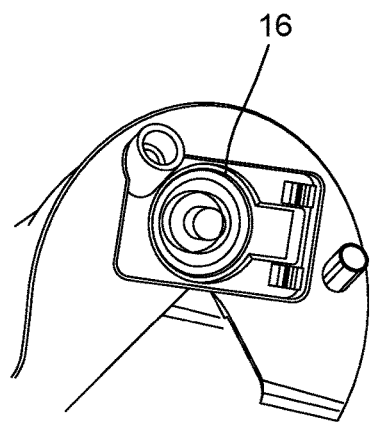
FIG. 4 shows a perspective view of the front part of the reservoir of the handpiece according to the embodiment of the invention.
Figure 5:
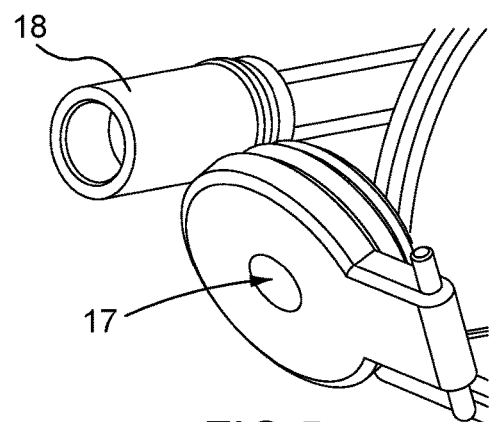
FIG. 5 shows a perspective view of the hatch of the reservoir of the handpiece according to the embodiment of the invention.

The reservoir 10 of the handpiece 1 is fixed removably in the rear part of the main body 3. As can be seen from FIGS. 2 and 3, this reservoir is fixed by a mechanical force fit 11 and/or mechanical clipping 12. It also comprises a recess 13 allowing it to be centred when fixed on the handpiece. In this embodiment, it is removable and refillable. For this purpose, it comprises a filling hatch 16 in its front part, as shown in FIG. 4. FIG. 5 illustrates such a hatch 16 which, on its surface, incorporates a microporous pellet 17 designed to allow air to pass through, but not the irrigation solution, so as to form an air inlet to the reservoir, by which it is possible to compensate for the vacuum left by the irrigation solution after it has been ejected through an outlet tube 18, thereby making it possible to maintain the internal pressure of the reservoir 10. Alternatively, the reservoir may not be removable and may simply be refilled directly on the handpiece.

Alternatively, the reservoir may be removable and disposable, being changed after each use of the handpiece, in order to ensure the sterilization and hygiene of the procedure.

Alternatively, the reservoir 10 could be fixed by any means to the main body. Its upper surface, visible to the practitioner, is transparent or comprises transparent zones, and it comprises graduations 15 allowing the practitioner to visualize and determine the quantity of irrigation solution remaining. In a variant, the surface of the reservoir 10 may have an anti-UV or anti-light treatment.

Moreover, according to this embodiment, the outlet tube 18 of the reservoir continues an internal part of the reservoir 10, as is shown in FIG. 6. A technical problem is to allow a continuous flow of the solution in all the positions taken up by the practitioner and, therefore, all the orientations of the handpiece and of its reservoir 10, in order to guarantee a constant irrigation of a root canal during the course of treatment. For this purpose, at least part of the tube inside the reservoir is made of a very flexible material and is ballasted by a weight 19, which makes it possible to keep it down in all the orientations of the handpiece and, consequently, to keep its end inside the irrigation solution. Alternatively, several tubes could be used whose ends would be arranged at different places in the reservoir 10.

Figure 24:
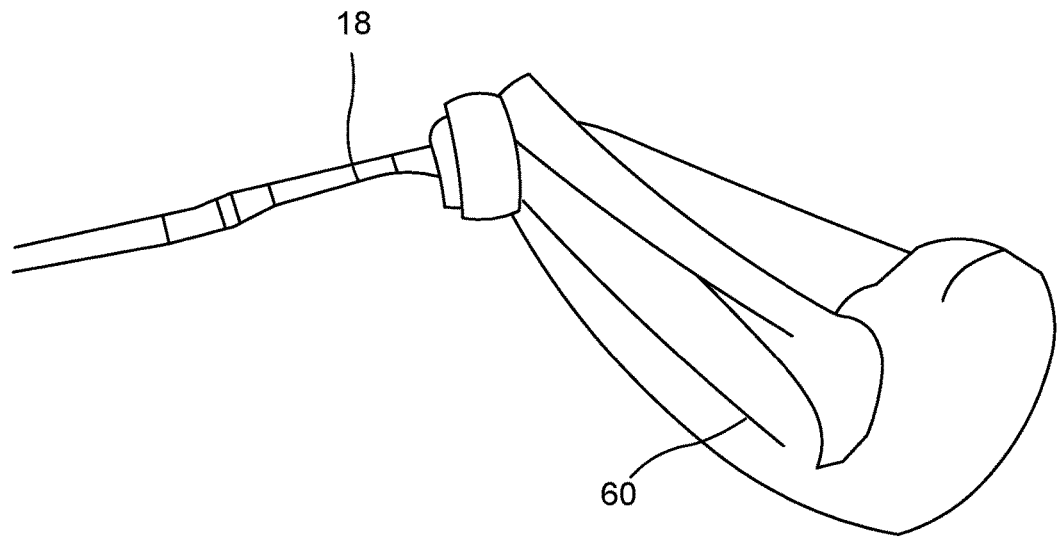
FIG. 24 shows a flexible pouch forming a reservoir of the handpiece according to a variant of the embodiment of the invention.

Alternatively, the reservoir 10 can incorporate a deformable flexible pouch 60, as shown in FIG. 24 by way of example, which comprises the irrigation solution. With such a configuration, the flexible pouch 60 deforms as the irrigation solution is used up, and its internal volume always corresponds to that of the irrigation solution present in the pouch. Therefore, a flexible pouch 60 of this kind never contains air, is airtight, contains only the irrigation solution in vacuo, and is able to guarantee the immersion of the aspiration zone in all the orientations of the handpiece, irrespective of the volume of solution held in the pouch. This pouch can be made of any flexible material, such as silicone or polyurethane. It can be filled with the aid of a syringe. Alternatively, the flexible pouch is removable and discardable. It can be changed after each use.

FIG. 7 illustrates a conduit 20 directly connected to the outlet tube 18 of the reservoir. This conduit 20 extends in a substantially longitudinal direction. At its two ends, it is provided with a duckbill 21 forming a joint, which is shown more specifically in FIG. 8 and which permits the orientation of the flow in just one direction. The irrigation solution enters through a first circular end 22 and leaves through the second end forming two lips 23.

Moreover, a pumping device is provided for conveying the irrigation solution from the reservoir 10 to the front end of the handpiece. In this embodiment, this pumping device is formed directly from the conduit 20, which is made of a deformable material, and by a movable roller 31, which can be seen in FIG. 9. More precisely, a portion of the conduit 20 is positioned between a movable roller 31 and a rigid support 32 of the movable body. A simple pressure on the movable roller 31 allows it to crush the conduit 20 against the rigid support 32, which creates an overpressure in the conduit 20 on account of its deformation, which is sufficient to expel at least some of the solution it contains towards the front of the handpiece, in the only direction of flow permitted by the abovementioned duckbills 21. Thereafter, when the movable roller recovers its initial position, in which it does not crush the conduit 20, the latter recovers its initial uncrushed volume, which is accompanied by an aspiration of the solution from the reservoir 10 into the conduit 20, so as to permanently maintain a sufficient quantity of solution in the conduit 20 for a subsequent expulsion.

Such a pumping device is thus realized by the cooperation between a portion of the conduit 20, delimited by two particular joints, and a device for crushing this portion of the conduit 20. This crushing device comprises a movable roller 31. It moreover comprises an irrigation motor 35 and an intermediate mechanism connecting this motor to the movable roller, so as to allow the movable roller 31 to be set in motion successively between its two end positions, i.e. a first position for crushing the conduit 20, then a second position for stopping this crushing action.

Figures 10, 11:
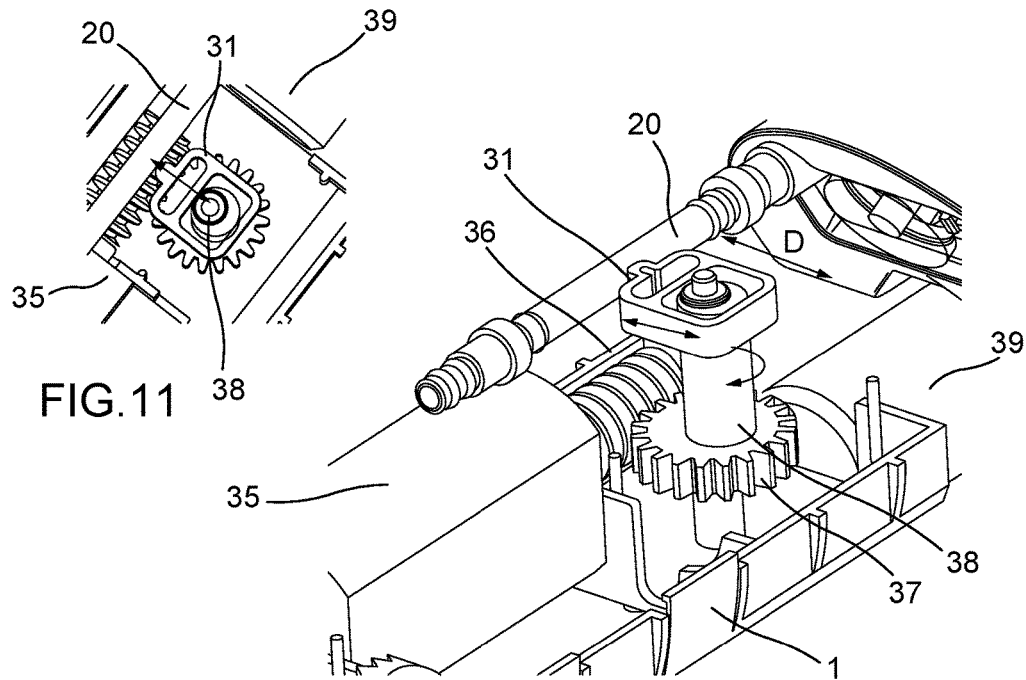
FIGS. 10 and 22 show a perspective view of the pumping mechanism of the irrigation device of the handpiece according to the embodiment of the invention.
FIG. 11 shows a plan view of the pumping mechanism of the irrigation device of the handpiece according to the embodiment of the invention.
Figure 22:
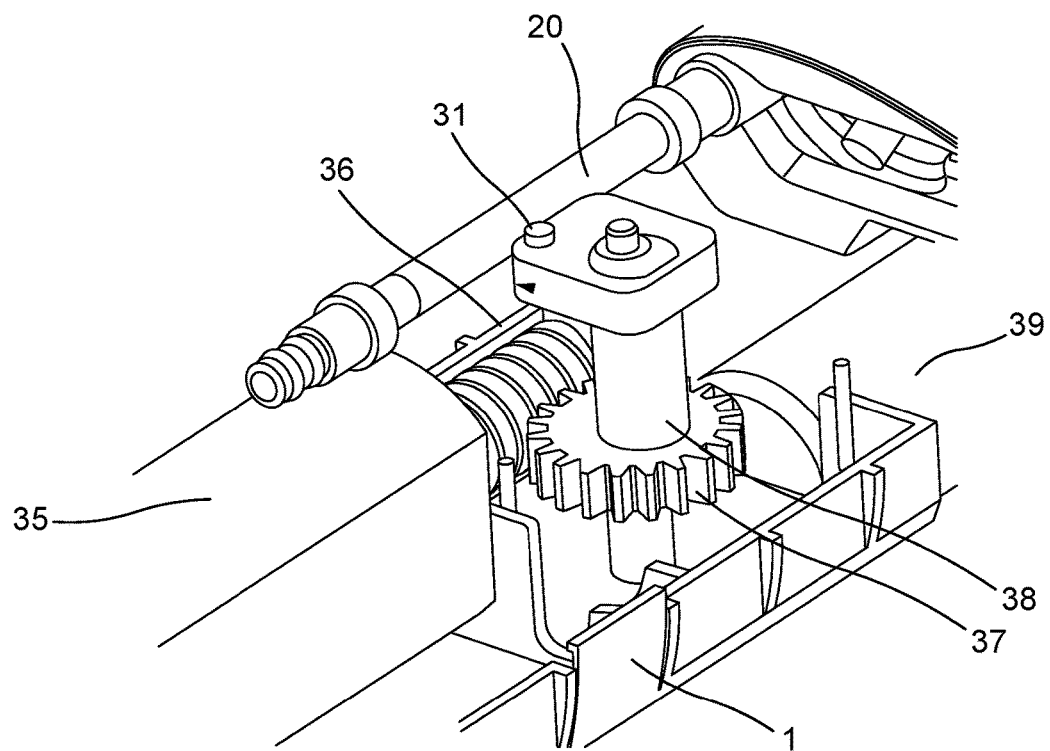

FIGS. 10, 22 and 11 illustrate in greater detail this intermediate mechanism according to the embodiment. An endless screw 36, which extends in a substantially longitudinal direction inside the main body of the handpiece, is arranged at the output of the irrigation motor 35. It cooperates with a wheel 37 movable in rotation about an axis substantially perpendicular to the longitudinal direction, said wheel 37 comprising an eccentric shaft 38 extending parallel to this axis of rotation. The end of this shaft 38 cooperates with an aperture arranged inside the movable roller 31. As this shaft 38 is eccentric, the rotation of the wheel 37 allows it to set the movable roller 31 in motion substantially in translation, in a direction D substantially perpendicular to the conduit 20, so as to occupy a first end position, in which it crushes the conduit 20, and a second end position, in which it releases the conduit 20. The movable roller 31 is preferably arranged in a guide device so as to guide its movement in translation between its two positions mentioned above, while at the same time ensuring that it is held within the main body of the handpiece. Finally, a rechargeable battery 39 is arranged in the main body of the handpiece in order to power the motor 35.

The pumping used by the device described above is such that it has to permit the delivery of the irrigation solution at a sufficient flow rate, for example at least 4 ml/min, or at least 6 ml/min, preferably between 6 and 10 ml/min according to this embodiment. Alternatively, this flow rate could assume any other value less than or equal to 10 ml/min. This flow rate could be regulated by the dentist by way of a flow regulation device. The pumping device thus described has the advantage of great simplicity, a small overall size and a low cost. This unit forming the pumping device can also be easily replaced, possibly by a dentist in his or her surgery, thus simplifying the maintenance of the handpiece. For this purpose, a hatch can be provided on the surface of the handpiece, in the area of the pumping device, in order to allow access to these components. For example, this hatch can be arranged in the surface of the handpiece serving as the rigid support 32. Alternatively, any other pump can be implemented.

Figures 12, 13:
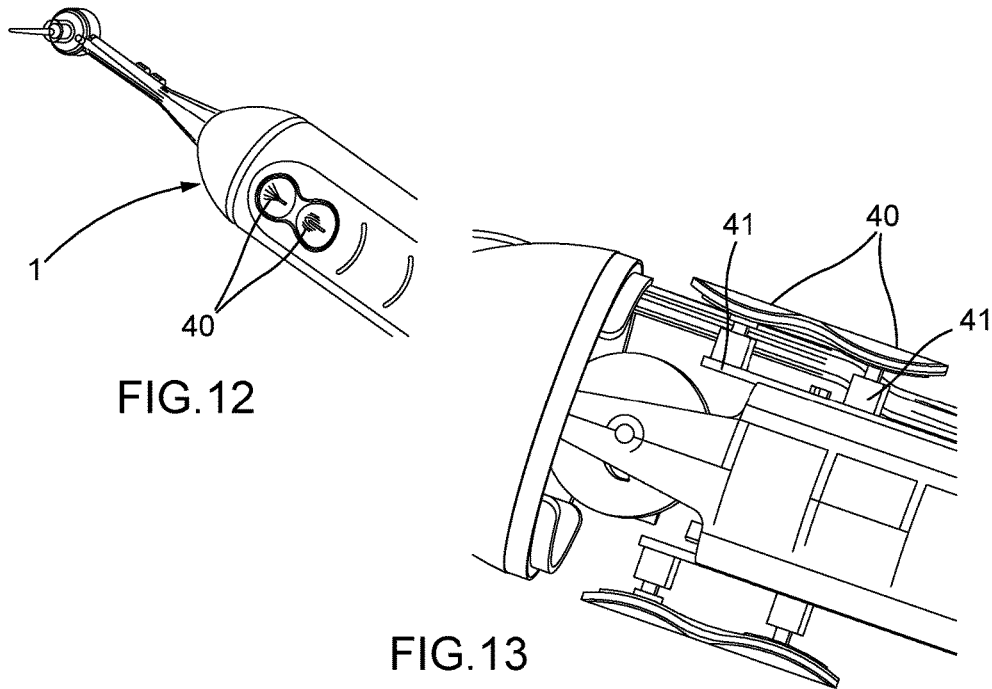
FIG. 12 shows a view of the control buttons of the handpiece according to the embodiment of the invention.
FIG. 13 shows an internal view of the handpiece revealing the function of the control buttons according to the embodiment of the invention.

The irrigation motor 35 is started up by way of at least one control button 40. In this embodiment, two control buttons 40 are overmoulded on the shell of the main body of the handpiece, as can be seen in FIGS. 12 and 13. The forming of these buttons by overmoulding has the advantage of guaranteeing leaktightness. Of course, any other type of actuating button may be suitable. As can be seen in particular from FIG. 12, each button 40 allows contactors 41 to be acted on by way of skins of flexible material. Pressure on a button 40 thus makes it possible to induce an electrical contact by way of these contactors 41.

Figure 14:
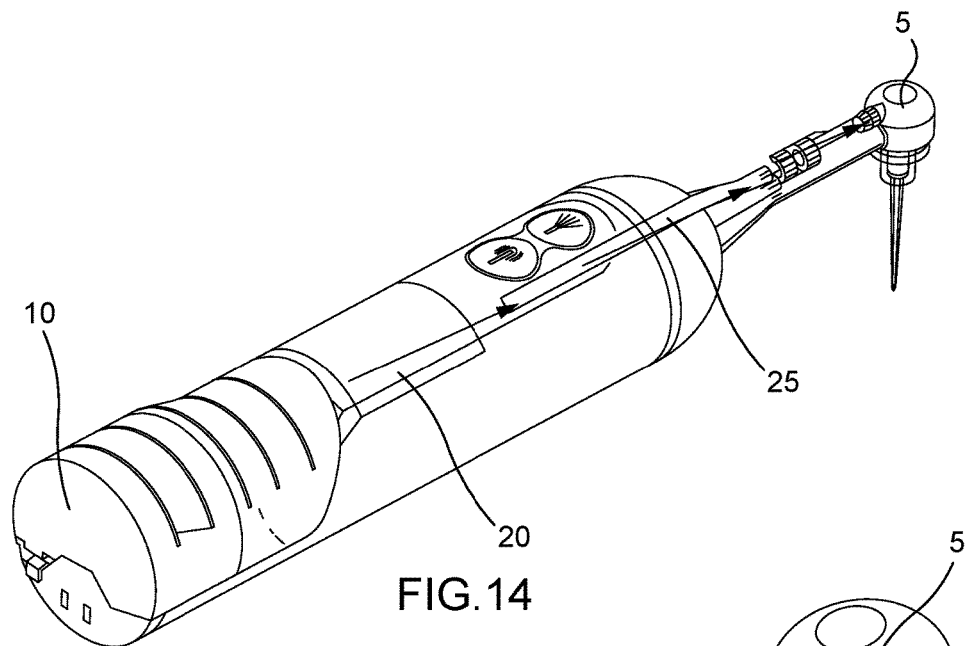
FIG. 14 shows a perspective side view of a handpiece and of its irrigation conduit according to the embodiment of the invention.
Figure 15:
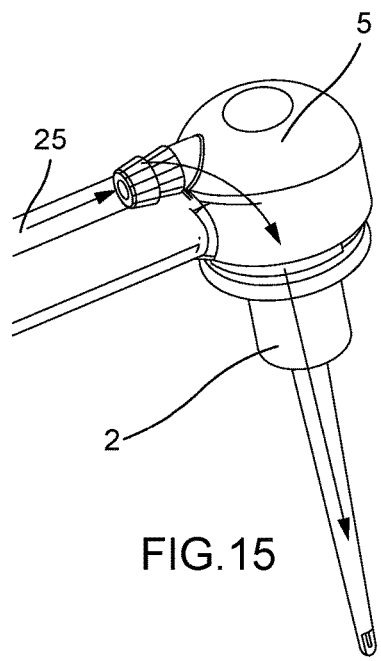
FIG. 15 shows a perspective view of the irrigation flow in the head of the handpiece according to the embodiment of the invention.

As is illustrated in FIGS. 14 and 15, the handpiece comprises an irrigation circuit for conveying the irrigation solution from the reservoir 10, positioned towards its rear end, to its endpiece 2 in the area of its front end. For this purpose, the conduit 20 mentioned above is then continued forwards by another conduit 25, which continues the delivery of the irrigation solution to the head 5 of the handpiece. Part of this conduit 25 is fixed on the outer surface of the handpiece in the area of the arm 4. Alternatively, it could be integrated inside this arm, by using an arm of slightly greater diameter. In the area of the head 5 of the handpiece, a tube allows the irrigation solution to be guided to a connection device for an endpiece 2 along a curve forming a quarter turn, so as to allow it to exit in a direction substantially perpendicular to the longitudinal direction. According to this embodiment, the endpiece 2 is hollow and allows the irrigation solution to be guided in it, at least along part of its length, so as to allow the solution leaving it to penetrate directly into the root canal that is to be irrigated. Alternatively, the irrigation solution could be conveyed differently to a root canal, for example by flowing on the outer surface of the endpiece instead of inside the latter, and/or could be guided in a manner at least partially independent of the endpiece 2, for example by being guided by the endpiece along only part of its length, or by way of an additional tube separate from the endpiece, substantially parallel thereto.

The handpiece according to the embodiment of the invention also uses a second important function of agitation, which entails setting the endpiece 2 in motion, which thus permits agitation of the irrigation solution in the root canal. The combination of the two functions in the same appliance is advantageous since it permits a combined action: the irrigation solution constantly replenished permits optimal irrigation, and its constant and simultaneous agitation permits its immediate and optimal action. This combination of actions permits a much better result to be achieved than that obtained with the solutions of the prior art, which separate these actions.

Figure 16:
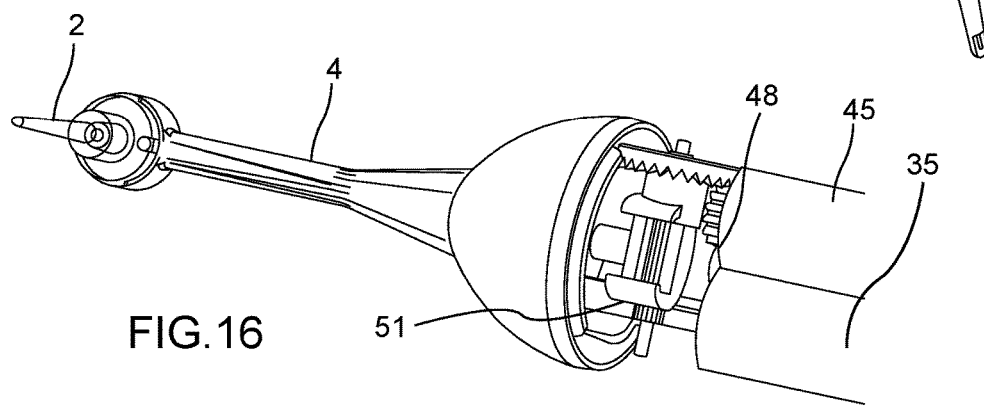
FIGS. 16 and 23 show a perspective view of the handpiece revealing the mechanism of the agitator device according to the embodiment of the invention.
Figure 23:
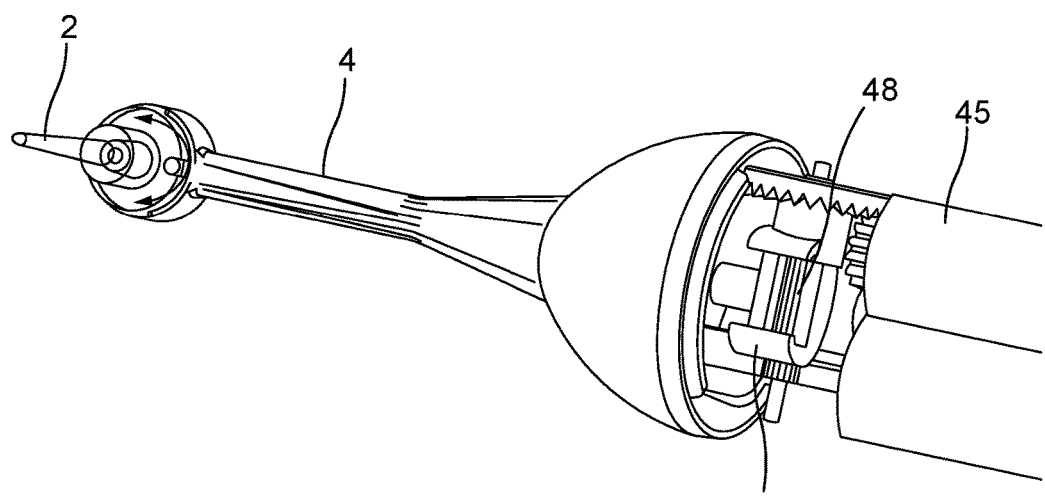

This agitation function is used by an agitator device comprising a second motor 45, which will be referred to as the agitation motor and can be seen in FIGS. 16 and 23, positioned partly in front of the main body of the handpiece, and which cooperates with a joining mechanism to the connector device under the head 5 of the handpiece, so as to be able to transmit a movement to an endpiece 2 fixed on this head by way of the connector device.

Figure 17:
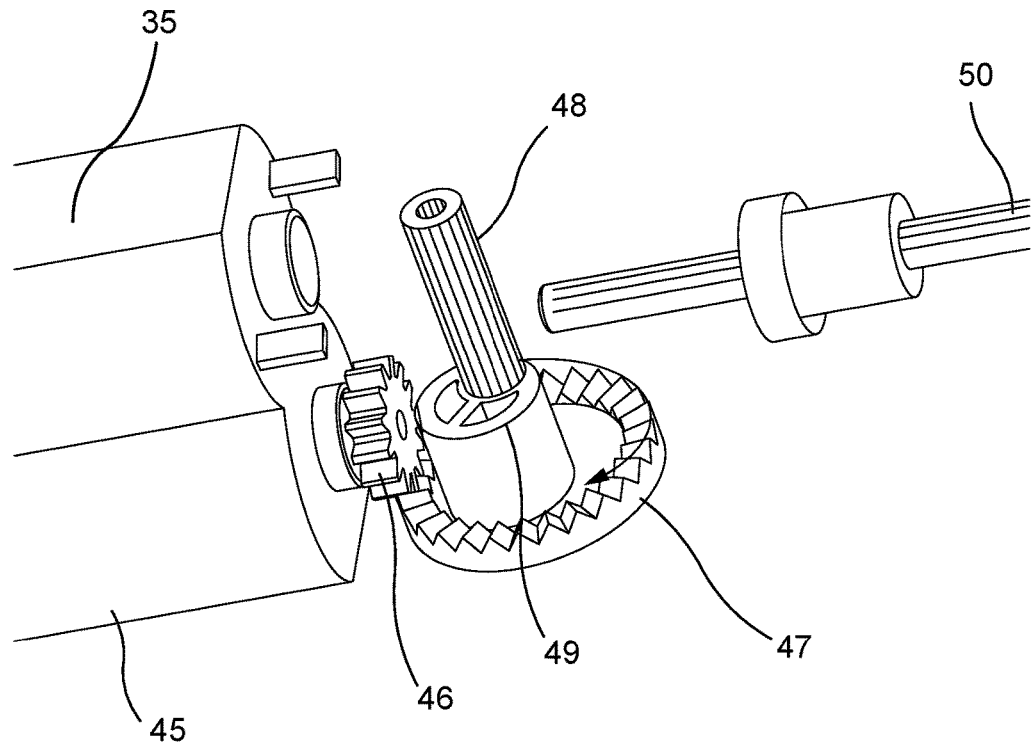
FIG. 17 shows a perspective view of the mechanism of the agitator device of the handpiece according to the embodiment of the invention.
Figure 18:
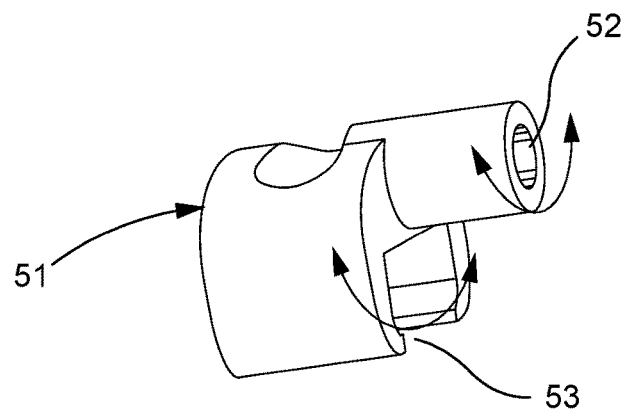
FIG. 18 shows a perspective view of a joining component of the mechanism of the agitator device of the handpiece according to the embodiment of the invention.

FIG. 17 illustrates more precisely the connection mechanism of the agitator device. The motor 45 acts first of all on a first wheel 46, which cooperates with a second wheel 47, set in rotation about an axis substantially perpendicular to the longitudinal direction. This second wheel 47 comprises a shaft 48 extending parallel to its axis of rotation and forming a shoulder 49, which cooperates with a longitudinal shaft 50, which extends in a direction substantially parallel to the axis of the handpiece, within the arm 4 thereof, as far as the head 5 of the handpiece. For this cooperation, the rear end of the longitudinal shaft 50 is connected to the shoulder by a joining component 51, shown in FIG. 18, which comprises a seat 52 for receiving the rear end of the shaft 50 and a joining part 53 for fixing it to the shoulder 49. This second wheel 47 with its shaft 48 and the shoulder 49 thus forms an asymmetrical toothed wheel, with which it is possible to induce a rocking movement of the shaft 50.

Figure 19:
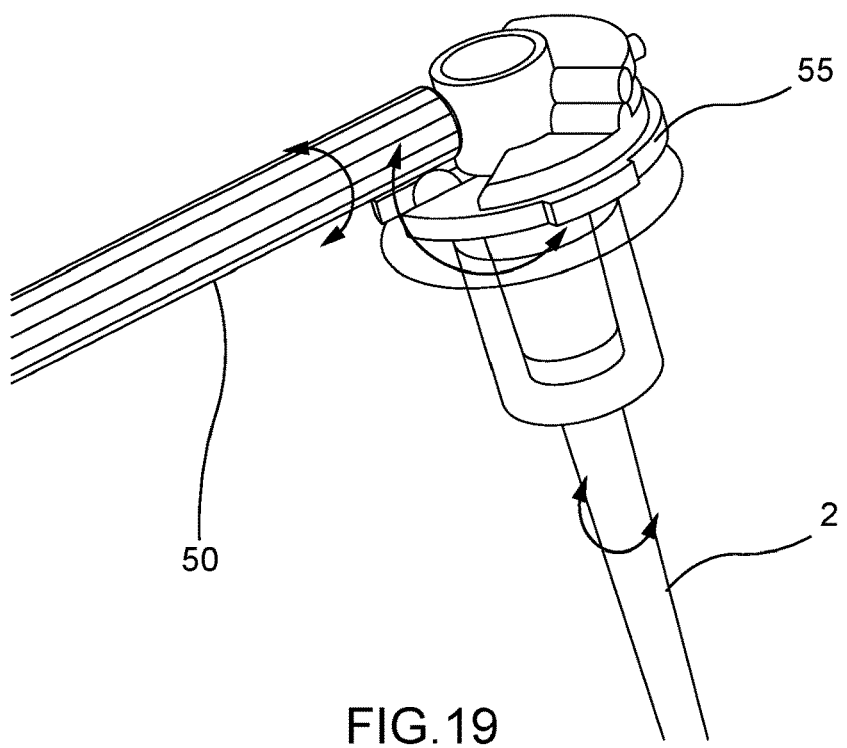
FIG. 19 shows a perspective view of the part of the agitator device arranged in the area of the head of the handpiece according to the embodiment of the invention.

FIG. 19 illustrates the front part of the agitator device, in the area of the head 5 of the handpiece. It comprises a component 55 movable in rotation about an axis substantially perpendicular to the shaft 50, connected to the front end of this shaft 50 by a drive stub. The rocking movements of the shaft 50 are transmitted to the component 55 and effect reciprocating movements of rotation in one direction then the other. According to the embodiment, the amplitude of the rocking movement allows the component to reach an amplitude of rotation of at least 90°, plus or minus 45° with respect to a central position, and preferably at least 270°, for example about a full turn. Alternatively, this amplitude or angular clearance can assume any other value, even a very much lower one, for example less than 20°. In its lower part, this component 55 has a connector device which permits a detachable connection to an endpiece 2. According to the embodiment, the speed of rotation is chosen between 2,500 and 4,000 movements per minute, for example about 3,120 rpm. This agitation is therefore far from the principle of ultrasonic agitation often implemented in the prior art. Alternatively, other types of movement are possible, such as movements of translation, possibly combined with rotations. Thus, the endpiece 2 is set in motion relative to the handpiece, in particular relative to the main body 3 thereof, which can serve as a reference point. This movement is preferably a rotation, advantageously a succession of rotations in one direction and the other, but possibly another form of movement. In all cases, movement will be understood here as a genuine movement of the endpiece relative to the handpiece, not just a vibration of the assembly. Moreover, this movement advantageously concerns the whole of the endpiece.

In the embodiment described, a rechargeable battery 49 is used and implemented in the main body of the handpiece. In this embodiment, the handpiece is equipped with a recharging device for this battery, formed in a rear part and provided to cooperate with a support base which moreover has a function of battery recharge. The handpiece is thus in the form of a wireless instrument that is particularly easy to manipulate. Alternatively, the handpiece can comprise a seat for electric batteries, or no internal power source, but rather a simple connector for connection to an external electrical source.

According to the embodiment, two control buttons 40 are provided in order to obtain the following operating modes:
- agitator device triggered in combination and simultaneously with the irrigation device, or
- the irrigation device is started on its own, or
- the agitator device is started on its own.

In all these operating modes, the handpiece requires continuous pressure on the one or more buttons for its operation, and it stops as soon as this pressure is released. Alternatively, the irrigation can be effected under permanent control of a button, while the agitation by contrast requires pressure to be applied twice in order to initiate it and stop it.

As was mentioned at the outset, the endpiece 2 is connected to the lower part of the head 5 by a connector device. This detachable connector can be secured by screwing, clips or a force fit. Thus, the endpiece 2 is disposable and is changed after each use. This mechanical connection moreover comprises a sealing means.

The endpiece 2 can have an axially offset or asymmetrical geometry, which enhances its effect in the root canal during use. It is made of a flexible material, so as to also amplify its effect during its rotation. Preferably, the material chosen is a compromise between sufficient rigidity, to be able to be placed in a root canal without risk of folding or breaking its point, and flexibility and/or pliability and/or elasticity sufficient to be able to adapt to the root canal anatomy which often has curvatures, and to be able to be driven in the root canal without risk of fracturing it or of causing damage to the root canal walls. For this purpose, a medical-grade plastic material formed integrally by injection is advantageous.

Alternatively, the endpiece could be made wholly or partially of metal, for example taking the form of a combination of plastic injected on a metallic part, with duplicate moulding technology, or by any other method of assembly such as adhesive bonding, for example. The metal part could, for example, form the central part of the endpiece and could be covered by an outer layer of plastic which would protect the walls of the root canal. As an additional alternative, the upper part of the endpiece, intended to be connected to the handpiece, could be made of injection-moulded plastic, while the lower part could be formed by an extruded plastic tube.

Figure 20:
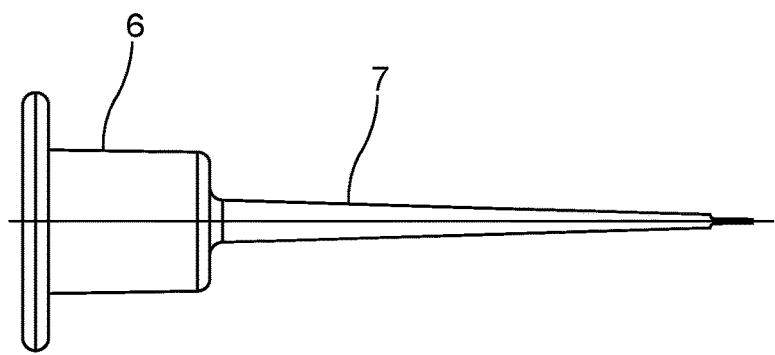
FIG. 20 shows a side view of an endpiece of the handpiece according to the embodiment of the invention.
Figure 21:
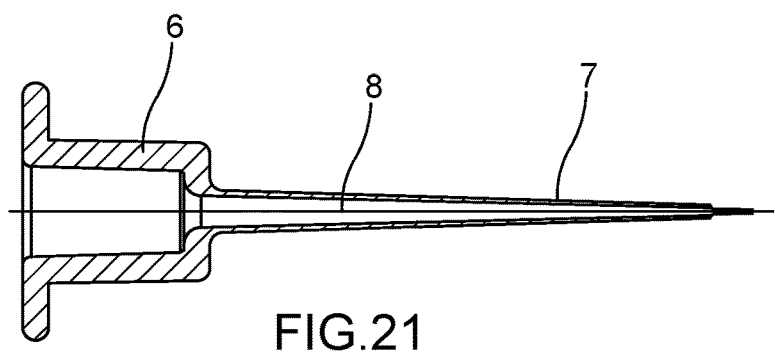
FIG. 21 shows a sectional side view of an endpiece of the handpiece according to the embodiment of the invention.

FIGS. 20 and 21 show an endpiece 2 according to an embodiment of the invention. This endpiece 2 comprises a joining part 6 with a connector element complementing the connector device provided on the head 5 of the handpiece. This joining part 6 has a substantially circular cross section, with a diameter of less than or equal to 5 mm, perhaps 3 mm, in order to obtain a small overall size. The endpiece 2 then comprises a lower part of the needle 7 type intended to penetrate a root canal. This needle has a conical shape, with an angle of approximately 5 or 6 degrees. It has a length of between 2 and 3 cm. Its lower end, the narrower one, has a diameter of less than or equal to 0.6 mm, perhaps 0.3 mm. This needle 7 is hollow over at least part of its length, so as to form an inner conduit 8 for the final guiding of the irrigation solution into a root canal, as has been mentioned above. Its outer surface can be smooth or can have raised areas, for example ribs, for increasing the agitation of the irrigation solution, or barbs or a helical rib for minimally aggressive friction. Alternatively, these raised areas can be formed by simple chemical embossing of the mould cavity forming the outer surface of the endpiece, which would then be slightly abrasive.

According to an alternative embodiment, the needle 7 of the endpiece 2 has a fusible zone allowing it to break in the event of excessive force, such as too great a curvature, in the area of this fusible zone, in order to avoid a situation where too small a part towards one end breaks off and remains accidentally blocked within a root canal.

Figure 25:
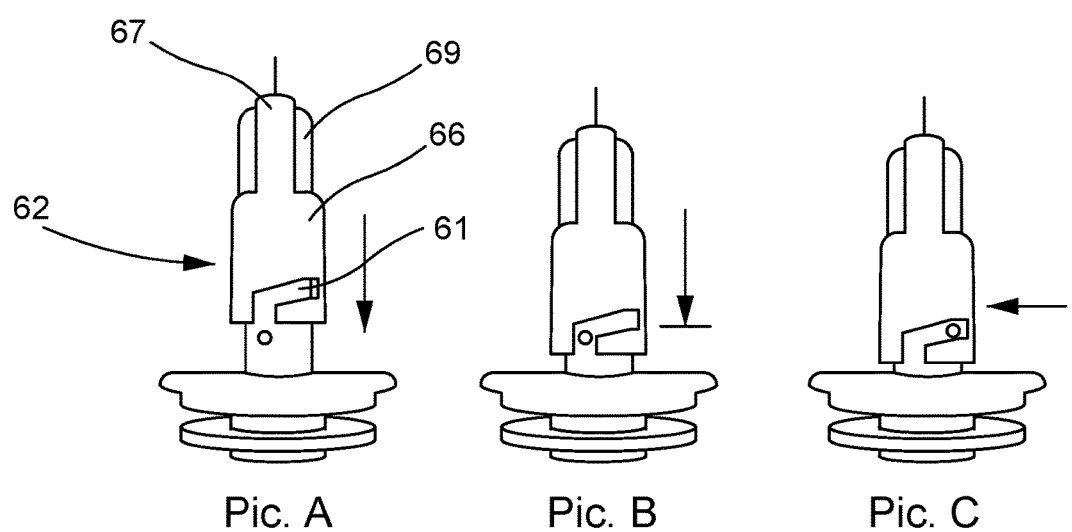
FIGS. 25a to 25c illustrate three steps in fixing an endpiece on the handpiece according to a variant of the embodiment of the invention.

FIGS. 25a to 25c show another variant of an endpiece 62 comprising a metal needle 67 with a first part of considerable diameter, ending in a second and much finer final part. A conduit (not shown) also passes through the needle for delivery of the irrigation solution. The first part is also provided with wings 69. The endpiece 62 moreover comprises a joining part 66 provided with an opening 61 for forming the female part of a bayonet-type connection. Complementing this, the head 5 of the handpiece is provided in its lower part with a matching connector element, for the use of this bayonet-type connection. Alternatively, the fixation can be effected by any other means, for example by simple screwing. This fixation can also comprise a slight axial offset in order to amplify the movement during its rotation.

Of course, the handpiece can have other forms and variants than those described above. In particular, the irrigation device and/or the agitator device can be of a different form. It is possible for only some of the elements of these devices to be integrated in the handpiece and to cooperate with an outer part.

Finally, the handpiece according to the invention has the following advantages:
- it is light, ergonomic and convenient and functions with simple buttons allowing use with either hand;
- it does not interact with tubes that get in the way, and it is therefore easy to manoeuvre;
- it combines several functions and does not require complementary operations in a separate phase with supplementary tools.

The invention claimed is:

1. Handpiece for endodontic treatment, comprising:
   an irrigation device for conveying an irrigation solution from a reservoir to a head for the purpose of ejecting the solution into a root canal, and
   an agitator device for setting in motion an endpiece intended to penetrate inside a root canal in order to promote the action of the irrigation solution,
   wherein a main body of the handpiece incorporates a first motor for the irrigation device,
   wherein the handpiece body incorporates a pumping device,
   wherein the first motor has a first actuation shaft oriented in a main longitudinal direction of the handpiece body, and the pumping device has a first transmission shaft oriented in a first transverse direction relative to the main longitudinal direction of the handpiece and actuated by the first actuation shaft of the first motor,
   wherein the first transmission shaft cooperates with a roller movable to press in a transverse direction relative to the main longitudinal direction of the handpiece on a deformable wall of a deformable conduit portion of at least one conduit for conveying an irrigation solution to an outlet of the handpiece, wherein the deformable conduit portion is oriented in the main longitudinal direction of the handpiece.

2. Handpiece according to claim 1, wherein the main body of the handpiece incorporates a second motor for the agitator device.

3. Handpiece according to claim 2, wherein the roller is movable between a first position, in which the roller presses the deformable conduit portion so as to induce the ejection of the irrigation solution that the latter contains, and a second position, in which the roller does not press the conduit portion, which generates a phenomenon of aspiration of the irrigation solution from the reservoir when the deformable conduit portion recovers its initial shape after it has been pressed by the movable roller.

4. Handpiece according to claim 2, wherein the second motor has a second actuation shaft oriented in a main longitudinal direction of the handpiece body, and the irrigation device comprises a joining mechanism, wherein the joining mechanism comprises:
   a second transmission shaft oriented in a second transverse direction relative to the main longitudinal direction of the handpiece and actuated by the second actuation shaft, wherein the second transmission shaft cooperates with an eccentric shoulder, and
   a joining component actuated by the shoulder and transforming the rotation movement of the eccentric shoulder in a rocking movement of a shaft oriented in the main longitudinal direction and connected to an endpiece, so as to transmit the rocking movement to the endpiece.

5. Handpiece according to claim 2, wherein the first motor and the second motor are superposed in a radial direction.

6. Handpiece according to claim 1, wherein the irrigation device comprises the reservoir.

7. Handpiece according to claim 6, wherein the reservoir is removable and comprises all or some of the following elements:
   a filling hatch; and/or
   a tube part arranged inside the reservoir and connected to a weight in order to guarantee the positioning of the tube part within an irrigation solution in all orientations of the handpiece; and/or
   graduations for visualizing the quantity of irrigation solution present in the reservoir; and/or
   a deformable flexible pouch containing the irrigation solution.

8. Handpiece for endodontic treatment according to claim 6, wherein the roller is movable between a first position, in which the roller presses the deformable conduit portion so as to induce the ejection of the irrigation solution that the latter contains, and a second position, in which the roller does not press the deformable conduit portion, which generates a phenomenon of aspiration of the irrigation solution from the reservoir when the deformable conduit portion recovers its initial shape after it has been pressed by the movable roller.

9. Handpiece according to claim 8, wherein the first motor for irrigation acts on a wheel of the first transmission shaft, wherein the first transmission shaft is an eccentric shaft which cooperates with the movable roller in order to position the roller successively in the first position and in the second position.

10. Handpiece according to claim 8, wherein the roller is movable between the first position and the second position in a direction transverse to the main longitudinal direction.

11. Handpiece according to claim 10, wherein the roller is movable translationally between the first position and the second position.

12. Handpiece for endodontic treatment according to claim 1, wherein the roller is movable between a first position, in which the roller presses the deformable conduit portion so as to induce the ejection of the irrigation solution that the latter contains, and a second position, in which the roller does not press the deformable conduit portion, which generates a phenomenon of aspiration of the irrigation solution from the reservoir when the deformable conduit portion recovers its initial shape after it has been pressed by the movable roller.

13. Handpiece according to claim 12, wherein the first motor for irrigation acts on a wheel of the first transmission shaft, wherein the first transmission shaft is an eccentric shaft which cooperates with the movable roller in order to position the roller successively in the first position and in the second position.

14. Handpiece according to claim 12, wherein the roller is movable between the first position and the second position in a direction transverse to the main longitudinal direction.

15. Handpiece according to claim 14, wherein the roller is movable translationally between the first position and the second position.

16. Handpiece according to claim 1, which comprises a conduit for guiding an irrigation solution to a head, and a device for connection to an endpiece, arranged in the area of the head.

17. Handpiece according to claim 1, wherein the agitator device comprises a second motor for agitation, and a joining mechanism between the second motor and a connection device in the area of a head of the handpiece in order to be able to fix and set in motion an endpiece connected to the handpiece.

18. Handpiece according to claim 17, wherein the joining mechanism comprises at least one wheel which acts on a shaft extending through an arm of the handpiece as far as the head, such that a front end of the arm effects rocking movements able to set in rotation an endpiece connected to the handpiece.

19. Handpiece according to claim 17, wherein the agitator device induces an alternating movement of rotation in one direction then another, with an angular clearance at least equal to 90°, of an endpiece connected to the handpiece.

20. Handpiece according to claim 17, wherein the agitator device induces a movement of rotation of an endpiece at a speed of between 2,500 and 4,000 movements per minute.

21. Handpiece according to claim 17, wherein the agitator device induces an alternating movement of rotation in one direction then another, with an angular clearance at least equal to 270°, of an endpiece connected to the handpiece.

22. Handpiece according to claim 1, which comprises at least one rechargeable battery arranged in a main body and connected to the first motor.

23. Handpiece according to claim 1, which comprises at least one control button overmoulded on a main body of the handpiece.

24. Handpiece according to claim 1, which comprises a removable endpiece, made at least partially of plastic or of metal.

25. Handpiece according to claim 24, wherein the endpiece is hollow along at least part of its length, so as to be able to form a conduit for an irrigation solution coming from a reservoir of the handpiece.

* * * * *